(12) United States Patent
York et al.

(10) Patent No.: US 9,883,782 B2
(45) Date of Patent: Feb. 6, 2018

(54) LIQUID FILTRATION VACUUM

(71) Applicant: Intelliclean Solutions, LLC, West Palm Beach, FL (US)

(72) Inventors: Larry D. York, McMinnville, TN (US); Randy G. Spencer, McMinnville, TN (US)

(*) Notice: Subject to any disclaimer, the term of this patent is extended or adjusted under 35 U.S.C. 154(b) by 100 days.

(21) Appl. No.: 15/133,146

(22) Filed: Apr. 19, 2016

(65) Prior Publication Data
US 2016/0227973 A1    Aug. 11, 2016

Related U.S. Application Data

(63) Continuation-in-part of application No. 14/885,975, filed on Oct. 16, 2015.
(Continued)

(51) Int. Cl.
| A47L 9/18 | (2006.01) |
|---|---|
| A47L 7/00 | (2006.01) |
| A61L 2/238 | (2006.01) |

(52) U.S. Cl.
CPC .............. *A47L 9/181* (2013.01); *A47L 7/0004* (2013.01); *A47L 7/0028* (2013.01); *A61L 2/238* (2013.01)

(58) Field of Classification Search
None
See application file for complete search history.

(56) References Cited

U.S. PATENT DOCUMENTS

| 1,839,582 A | 1/1932 | Nordhem |
|---|---|---|
| 2,250,226 A | 7/1941 | Juelson |
| (Continued) | | |

FOREIGN PATENT DOCUMENTS

| CN | 1541604 | 11/2004 |
|---|---|---|
| CN | 201542558 | 6/2006 |
| (Continued) | | |

OTHER PUBLICATIONS

Patent Cooperation Treaty, "International Search Report and Written Opinion," issued on Jul. 12, 2016, by Blaine R. Copenheaver, Authorized Office, in international application No. PCT/US2016/028313, document of 10 pages.

*Primary Examiner* — Duane Smith
*Assistant Examiner* — Phillip Shao
(74) *Attorney, Agent, or Firm* — Larson & Larson, P.A.; Justin P. Miller; Patrick A. Reid

(57) ABSTRACT

According to one embodiment, an upright liquid filtration vacuum cleaner includes a vacuum nozzle head and a housing moveably coupled to the vacuum nozzle head. The vacuum cleaner further includes a liquid tank that includes a wall defining an interior volume and a tank intake channel positioned in the interior volume. The interior volume is configured to hold a liquid. The tank intake channel is positioned to direct debris received from an intake passageway into the liquid tank so that the liquid in the interior volume of the liquid tank filters the debris into the liquid so that clean air is exhausted. The vacuum cleaner further includes a separator configured to generate an airflow. The vacuum cleaner is configured to seal the intake passageway when the vacuum cleaner is deactivated and further configured to unseal the intake passageway when the vacuum cleaner is activated.

20 Claims, 11 Drawing Sheets

Related U.S. Application Data

(60) Provisional application No. 62/122,300, filed on Oct. 16, 2014.

(56) References Cited

U.S. PATENT DOCUMENTS

| | | | |
|---|---|---|---|
| 2,693,000 A | 11/1954 | Minerley | |
| 2,886,125 A | 5/1959 | Denker | |
| 2,954,095 A | 9/1960 | Brock | |
| 3,065,316 A | 11/1962 | Olson | |
| 3,318,075 A | 5/1967 | Wilson | |
| 4,290,784 A | 9/1981 | Rawicki | |
| 4,487,746 A | 12/1984 | Tahiliani | |
| 4,545,410 A | 10/1985 | Paul et al. | |
| 4,678,485 A | 7/1987 | Finley et al. | |
| 4,693,734 A * | 9/1987 | Erickson, Jr. | A47L 5/365 |
| | | | 15/353 |
| 4,818,259 A | 4/1989 | Marano | |
| 4,874,404 A | 10/1989 | Boswell | |
| 4,939,809 A | 7/1990 | Park | |
| 5,189,757 A | 3/1993 | Williams et al. | |
| 5,199,963 A * | 4/1993 | Scarp | A47L 9/181 |
| | | | 55/320 |
| 5,215,560 A | 6/1993 | Lee | |
| 5,354,347 A | 10/1994 | McCoy et al. | |
| 5,752,997 A | 5/1998 | Roth | |
| 5,869,323 A | 2/1999 | Horn | |
| 5,873,143 A | 2/1999 | Huey | |
| 6,243,912 B1 * | 6/2001 | Grey | A47L 7/0009 |
| | | | 15/320 |
| 6,361,587 B1 | 3/2002 | Rohn et al. | |
| 6,379,439 B1 | 4/2002 | Shimizu | |
| 6,508,867 B2 | 1/2003 | Schoenewald et al. | |
| 6,553,614 B1 * | 4/2003 | Leon | A47L 7/0028 |
| | | | 15/353 |
| 6,776,824 B2 | 8/2004 | Wen | |
| 6,866,705 B2 * | 3/2005 | Nielsen | A47L 9/102 |
| | | | 15/353 |
| 7,644,470 B2 | 1/2010 | Lee et al. | |
| 7,819,127 B1 | 10/2010 | Huffman | |
| 8,728,222 B2 | 5/2014 | Kim et al. | |
| 8,753,438 B2 | 6/2014 | Dallas et al. | |
| 8,881,344 B2 | 11/2014 | Akin | |
| 2003/0229964 A1 * | 12/2003 | Thomason | A47L 5/28 |
| | | | 15/353 |
| 2005/0108849 A1 | 2/2005 | Lam | |
| 2005/0198763 A1 * | 9/2005 | Lee | A47L 5/225 |
| | | | 15/320 |
| 2006/0130265 A1 | 6/2006 | Oh et al. | |
| 2006/0174438 A1 | 8/2006 | Ji et al. | |
| 2006/0225242 A1 | 10/2006 | Oh et al. | |
| 2006/0260088 A1 * | 11/2006 | Nam | A47L 5/225 |
| | | | 15/320 |
| 2011/0303244 A1 | 12/2011 | Faragher | |
| 2016/0051107 A1 | 2/2016 | Saltiel-Gonsen et al. | |

FOREIGN PATENT DOCUMENTS

| | | |
|---|---|---|
| CN | 201131707 | 10/2008 |
| CN | 201701153 | 1/2011 |
| CN | 204478276 | 7/2015 |
| ES | 1061988 | 5/2006 |
| WO | 2014/162165 | 10/2014 |

* cited by examiner

LIQUID FILTRATION VACUUM

CROSS-REFERENCE TO RELATED APPLICATIONS

This application is a continuation-in-part of pending U.S. patent application Ser. No. 14/885,975, filed Oct. 16, 2015, which claims the benefit of U.S. Provisional Application No. 62/122,300, filed Oct. 16, 2014, which are hereby incorporated by reference in their entireties.

TECHNICAL FIELD

The present disclosure pertains to the field of vacuum cleaners and more particularly to a liquid filtration vacuum.

BACKGROUND

There are available today various types of vacuum cleaners. One type of vacuum cleaner is a canister type. Canister type vacuum cleaners typically have a relatively stationary canister which is connected to a movable wand by a flexible connecting hose. Another type of vacuum cleaner is an upright-style vacuum cleaner. Upright-style vacuum cleaners are typically integrated units having an inlet, a filter, bag, and/or canister, and a handle connected together vertically in a single, portable unit. Upright-style vacuum cleaners may provide greater versatility and convenience than canister type vacuum cleaners because the upright-style vacuum cleaner is an integrated unit that can be moved and maneuvered by a single handle.

Traditional vacuum cleaners typically utilize mechanical filters to filter dirt and debris from directed airflow before returning the filtered air into the atmosphere. Some vacuum cleaners use bags to collect the dirt and debris, while some utilize a bin collection system. Vacuum cleaners that use bags, bins, and/or other mechanical filters lose efficiency with each use because dirt and dust captured by these components can clog the ports that allow air to flow through them. As a result, mechanical filters have to be replaced regularly, and still send germs, bacteria and dust back into the atmosphere when in use. Those who suffer breathing disorders such as asthma or have allergies are especially vulnerable. Purchasing mechanical filters and vacuum bags can make any vacuum cleaner very expensive to use and operate over time. Vacuum bags create germs and bacteria, as well as smell and lose efficiency. As such, traditional vacuum cleaners may be deficient.

SUMMARY

According to one embodiment, an upright liquid filtration vacuum cleaner includes a vacuum nozzle head and a housing moveably coupled to the vacuum nozzle head. The movable coupling is configured to allow the housing to tilt backwards with respect to the vacuum nozzle head. The vacuum cleaner further includes a liquid tank that is removably insertable into the housing. The liquid tank includes a wall defining an interior volume and a tank intake channel positioned in the interior volume. The interior volume is configured to hold a liquid. The tank intake channel is in fluid communication with an intake passageway that extends from the tank intake channel to an opening in the vacuum nozzle head. The tank intake channel is further positioned to direct debris received from the intake passageway into the liquid tank such that the liquid in the liquid tank can filter the debris into the liquid so that clean air is exhausted. The vacuum cleaner further includes a motor coupled to the housing and a separator coupled to the housing and the motor. The separator is in fluid communication with the interior volume of the liquid tank. The separator is configured to generate an airflow and further configured to prevent the liquid from being exhausted out of the interior volume of the liquid tank through the separator. The vacuum cleaner is configured to seal the intake passageway when the vacuum cleaner is deactivated so as to prevent the liquid from leaking out of the interior volume of the liquid tank through the intake passageway. The vacuum cleaner is further configured to unseal the intake passageway when the vacuum cleaner is activated so as to allow the debris to be received in the interior volume of the liquid tank from the intake passageway. The vacuum cleaner is configured to operate as a wet vacuum in which the debris comprises a liquid to be extracted. The vacuum cleaner is further configured to operate as a dry vacuum in which the debris comprises a non-liquid matter.

In some embodiments, the vacuum cleaner is devoid of a dry, mechanical filter.

In some embodiments, the vacuum cleaner includes a dry, mechanical filter.

In some embodiments, the tank intake channel is further positioned to direct the debris received from the intake passageway to below a liquid level of the liquid.

In some embodiments, the tank intake channel is further positioned to direct the debris received from the intake passageway to above a liquid level of the liquid.

In another embodiment, an upright liquid filtration vacuum cleaner includes a vacuum nozzle head and a housing moveably coupled to the vacuum nozzle head. The movable coupling is configured to allow the housing to tilt backwards with respect to the vacuum nozzle head. The vacuum cleaner further includes a liquid tank that is removably insertable into the housing. The liquid tank includes a wall defining an interior volume and a tank intake channel positioned in the interior volume. The interior volume is configured to hold a liquid. The tank intake channel is in fluid communication with an intake passageway that extends from the tank intake channel to an opening in the vacuum nozzle head. The tank intake channel is further positioned to direct debris received from the intake passageway to below a liquid level of the liquid. The vacuum cleaner further includes a sealing flap positioned at a location in the intake passageway. The sealing flap has a first position configured to seal the intake passageway so as to prevent the liquid from leaking out of the interior volume of the liquid tank through the intake passageway. The sealing flap also has a second position configured to open the seal of the intake passageway so as to allow the debris to be received in the interior volume of the liquid tank from the intake passageway such that the liquid in the liquid tank can filter the debris into the liquid so that clean air is exhausted. The vacuum cleaner further includes a motor coupled to the housing, and a separator coupled to the housing and the motor. The separator is in fluid communication with the interior volume of the liquid tank. The separator is configured to generate an airflow and is further configured to prevent the liquid from being exhausted out of the interior volume of the liquid tank through the separator. The vacuum cleaner is configured to move the sealing flap from the first position to the second position when the vacuum cleaner is activated. The vacuum cleaner is further configured to move the sealing flap from the second position to the first position when the vacuum cleaner is deactivated. The vacuum cleaner is configured to operate as a wet vacuum in which the debris comprises a liquid to be extracted, and further configured to operate as a dry vacuum in which the debris comprises a non-liquid matter.

In some embodiments, the wall of the water tank includes antimicrobial particles. In some embodiments, the antimicrobial particles comprise micro silver particles. In some embodiments, the antimicrobial particles comprise nano silver particles.

In some embodiments, the liquid tank further includes a second tank intake channel positioned in the interior volume. The second tank intake channel is in fluid communication with a second intake passageway that extends from the second tank intake channel to the opening in the vacuum nozzle head. The second tank intake channel is further positioned to direct debris received from the second intake passageway to below the liquid level of the liquid. The vacuum cleaner further includes a second sealing flap positioned at a location in the second intake passageway. The second sealing flap has a first position configured to seal the second intake passageway so as to prevent the liquid from leaking out of the interior volume of the liquid tank through the second intake passageway. The second sealing flap also has a second position configured to open the seal of the second intake passageway so as to allow the debris to be received in the interior volume of the liquid tank from the second intake passageway. The vacuum cleaner is further configured to move the second sealing flap from the first position to the second position when the vacuum cleaner is activated, and further configured to move the second sealing flap from the second position to the first position when the vacuum cleaner is deactivated.

In some embodiments, both the intake passageway and the second intake passageway are positioned in the housing in locations behind the water tank.

In some embodiments, the intake passageway and the second intake passageway are positioned in the housing in locations opposite from each other.

In some embodiments, the vacuum cleaner further includes an automated flap mover configured to move the sealing flap from the first position configured to seal the first intake passageway so as to prevent the liquid from leaking out of the interior volume of the liquid tank through the intake passageway to the second position configured to open the seal of the intake passageway so as to allow the debris to be received in the interior volume of the liquid tank from the intake passageway. In some embodiments, the automated flap mover is a solenoid. In some embodiments, the vacuum cleaner further includes one or more movement resistors coupled to the sealing flap and configured to resist the movement of the sealing flap from the first position to the second position. The strength of the one or more movement resistors is configured to be overcome by the automated flap mover, the airflow, or both the automated flap mover and the airflow.

In some embodiments, the vacuum cleaner further includes one or more movement resistors coupled to the sealing flap and configured to resist the movement of the sealing flap from the first position to the second position. The strength of the one or more movement resistors is configured to be overcome by the airflow.

In some embodiments, the one or more movement resistors comprise one or more springs.

In some embodiments, the vacuum nozzle head includes a second motor coupled to a rotatable brush.

In some embodiments, the movable coupling is further configured to allow the housing to tilt backwards with respect to the vacuum nozzle head from a substantially upright position to a substantially horizontal position.

In another embodiment, a water filtration vacuum includes a micro silver (or nano silver) permeate for anti-bacterial and anti-fungal properties. The water filtration vacuum device draws in the air, forcing it into the water and mixing it with microbial nanoparticles (e.g., micro silver), returning clean, fresh water-washed, substantially purified air into the home environment.

In another embodiment, a water filtration vacuum cleaner comprises an upright-style vacuum cleaner having, among other things, a water tank and intake tubes for directing drawn air from the vacuum cleaner inlet to tank intake channels in the water tank. The tank intake channels extend below the water level such that intake air is exhausted from the tank intake channels directly into the water.

In some embodiments, the water tank includes reversible seals for sealing against the intake tubes while the vacuum cleaner is not operating, to prevent water from leaking out through the intake tubes. The reversible seals open when the vacuum cleaner is operating and there is airflow through the intake tubes.

In some embodiments, micro silver or nano silver particles are molded into the inner wall of the water tank for contacting the air in the water tank.

In another embodiment, an upright water filtration vacuum contains an antimicrobial particulate for anti-bacterial and anti-fungal properties. The water filtration vacuum device draws in the air, forcing it into the water and mixing it with, e.g., micro silver or nano silver particles, returning clean, fresh air into the home environment.

In another embodiment, a water-filter vacuum cleaner is provided having micro silver or nano silver impregnated qualities.

In another embodiment, a water-filter vacuum cleaner is provided in which the exhausted air is free of bacteria.

In another embodiment, a water-filter vacuum cleaner is provided where all the dirt is sucked into the water and captured and mixed with the micro silver or nano silver particles for antibacterial and antifungal properties.

In another embodiment, an upright-style vacuum cleaner is provided having a liquid-tight liquid filter incorporated into the vertical assembly.

BRIEF DESCRIPTION OF THE FIGURES

For a more complete understanding of the present disclosure and its features and advantages, reference is now made to the following description, taken in conjunction with the accompanying drawings, in which:

FIG. 1 is a front view of an example vacuum cleaner;

FIG. 2 is a perspective view of the vacuum cleaner of FIG. 1;

FIG. 3 is a rear elevation view of the vacuum cleaner of FIG. 1;

FIG. 4 is a side view of the vacuum cleaner of FIG. 1;

FIG. 5 is an additional front view of the vacuum cleaner of FIG. 1;

FIG. 6 is a detailed side view of an exemplary water tank intake of the vacuum cleaner of FIG. 1;

FIG. 7 is a side view of an example sealing flap and movement resistor positioned within the vacuum cleaner of FIG. 1;

FIG. 8 is a front view of an example sealing flap and movement resistor for a vacuum cleaner;

FIG. 9 is a is a side view of the sealing flap and movement resistor of FIG. 8;

DETAILED DESCRIPTION OF THE EXEMPLARY EMBODIMENTS

Examples of the present disclosure are best understood by referring to FIGS. 1-15 of the drawings, like numerals being used for like and corresponding parts of the various drawings.

Figure 1:
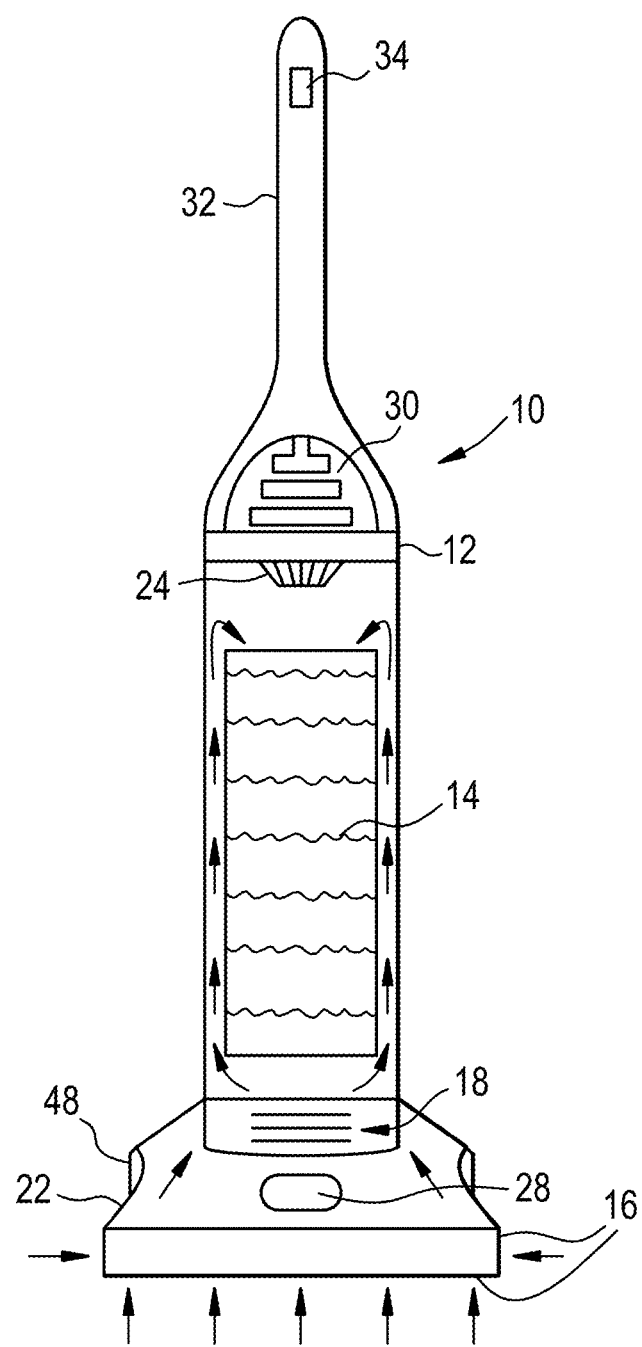
Figure 2:
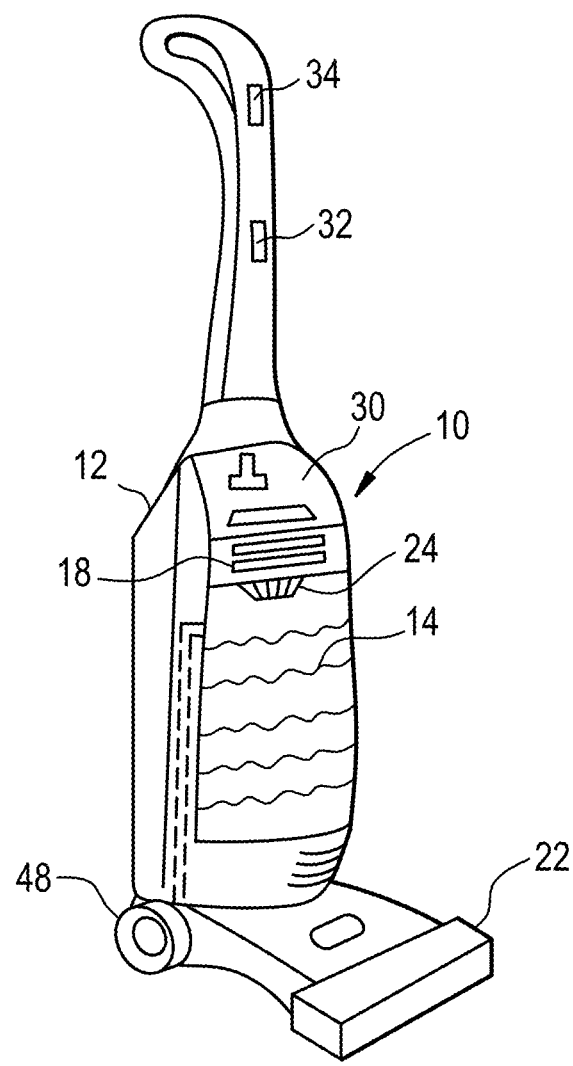

Referring now to the figures and particularly to FIG. 1, there is shown an exemplary upright vacuum cleaner 10 having housing 12. Removably contained within housing 12 is water tank or filtration liquid tank 14. In an exemplary embodiment, the water tank 14 is easily removable from housing 12 to enable the convenient removal and replacement of liquid therein. The water tank 14 may have any shape and/or size. For example, the water tank 14 may be, for example 8-14 inches tall and 6-8 inches wide. The water tank 14 may be a 1.5-2 quart water tank, in some examples. Motor 20 (FIG. 4) is positioned within (or otherwise supported by) the housing 12.

The water tank 14 may include liquid (such as water) that contacts the air flow into the vacuum cleaner 10 and removes debris. For example, the vacuum cleaner may direct incoming air and debris into contact with the liquid, which is typically water that absorbs the debris. Air flow through the water tank 14 also causes the liquid to circulate or agitate, which increases the efficiency of the absorption. In some examples, the use of liquid as a filter (as opposed to a dry, mechanical filter) may have a significant advantage in that the vacuum cleaner 10 uses readily available water, thereby eliminating the need for replaceable filters. In addition, the liquid in the water tank 10 may provide a room humidifying effect since some of the water may become vaporized in the air discharged from the vacuum cleaner 10 during use.

Further shown is vacuum cleaner handle 32 (which may telescope up and down) and compartment 30 for storing attachments typically used with vacuum cleaners (such as attachment brushes, nozzles, extensions, etc.). Vacuum nozzle head 22 contains a brushing unit (not shown in FIG. 1) typically contained in vacuum cleaners for brushing carpet free of debris, and may further include a rubber squeegee (for cleaning hard wood floors, for example). Suction and airflow motor 28 is supported in vacuum nozzle head in standard fashion. Suction and airflow motor 28 may rotate the brushing unit (causing the vacuum nozzle head 22 to be a power nozzle). Wheels 48 are located on the four corners of vacuum nozzle head 22 providing smooth rolling support of vacuum cleaner 10. In other embodiments, other wheel and support arrangements may be used.

Figure 15:
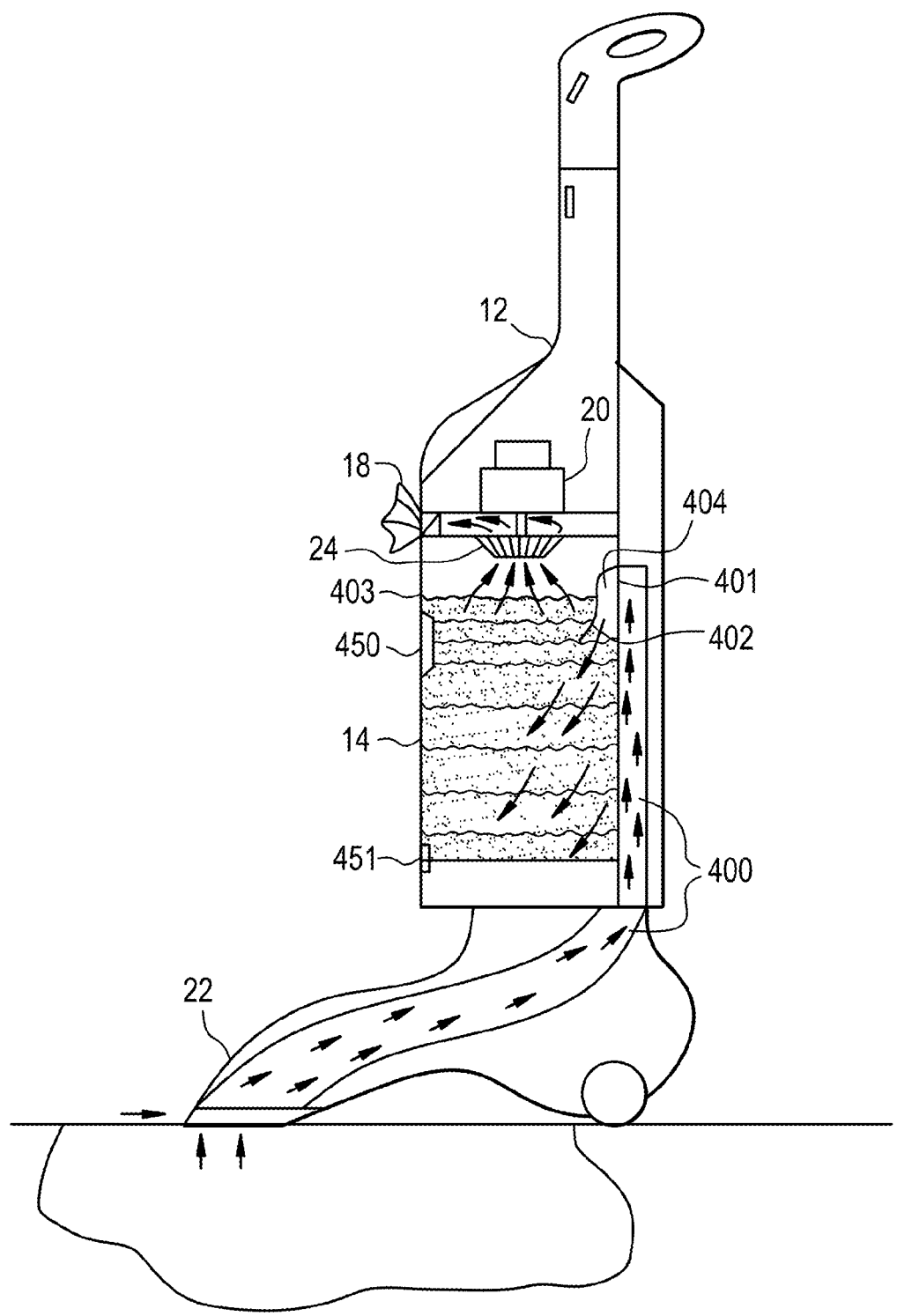
FIG. 15 is a side view of an example vacuum cleaner that can operate as a wet vacuum.

In operation, switch 34 initializes motor 20 of vacuum cleaner 10 creating an airflow and suction force (vacuum) sufficient to draw air (shown by arrows) entrained with debris. The debris can be any non-liquid matter, such as dust, dirt, particulates, microbes, and/or contaminants, or as is seen in FIG. 15, liquid matter, such any liquid whether spilled or intentionally dispersed on a surface to be vacuumed. The air entrained with debris can be drawn in through the vacuum nozzle head 22 and the inlet ports 16 and into contact with the liquid filter water tank 14. Motor 20 contained within housing 12 operates separator 24, rotating the separator 24 to speeds up to 16,000 rpm, for example, and forcing the debris to mix with water in water tank 14. By mixing the debris with the water, the debris is absorbed into the water and is prevented from being exhausted from the water tank 14. Additionally, separator 24 may draw and separate the clean exhaust air from the heavier water and particulates. The liquid filter water tank 14 may utilize one or more known liquid agents with filtration qualities, but contains water in an exemplary embodiment.

Figure 4:
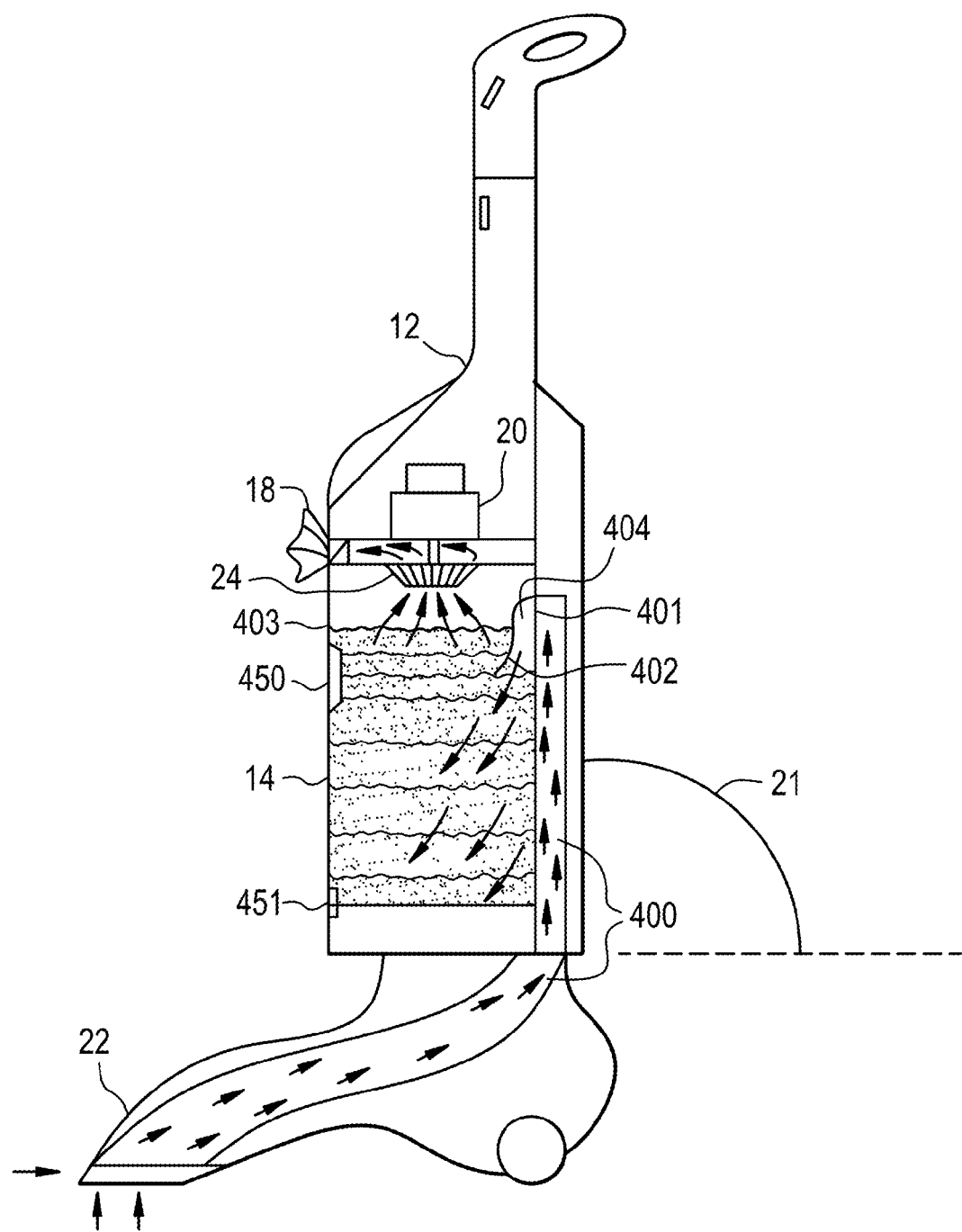

The housing 12 may be moveably coupled to the vacuum nozzle head 22. For example, the housing 12 may be tilted (or otherwise moved) with respect to the vacuum nozzle head 22. As is illustrated in FIG. 4, the housing 12 may be titled backwards from an upright position with respect to the vacuum nozzle head 22 by a tilting angle 21. Tilting angle 21 may be any angle. As an example, tilting angle 21 may allow housing 12 to be tilted backwards from an upright position (e.g., 90°) or a substantially upright position (e.g., 90°+/−10°) to a horizontal position (e.g., 0°) or a substantially upright position (e.g., 0°+10°). As other examples, tilting angle 21 may allow housing 12 to be tilted backwards from 90°-20°, substantially 90°-substantially 20°, 90°-30°, substantially 90°-substantially 30°, 90°-45°, substantially 90°-substantially 45°, or any other angle. The housing 12 may be tilted with respect to the vacuum nozzle head 22. Thus, even when the housing 12 is tilted, the vacuum nozzle head 22 may remain in the same upright position (shown in FIG. 4).

Tilting of the housing 12 may be accomplished by pressing a button or lever positioned on the housing 12 or the vacuum nozzle head 22, or the housing 12 may tilt freely with respect to the vacuum nozzle head 22. This button or lever may release the housing 12, allowing housing 12 to be tilted. When the housing 12 is tilted, all of the components of the housing 12 (including the water tank 14) may be titled at the same (or substantially the same) angle as the housing 12.

Figure 6:
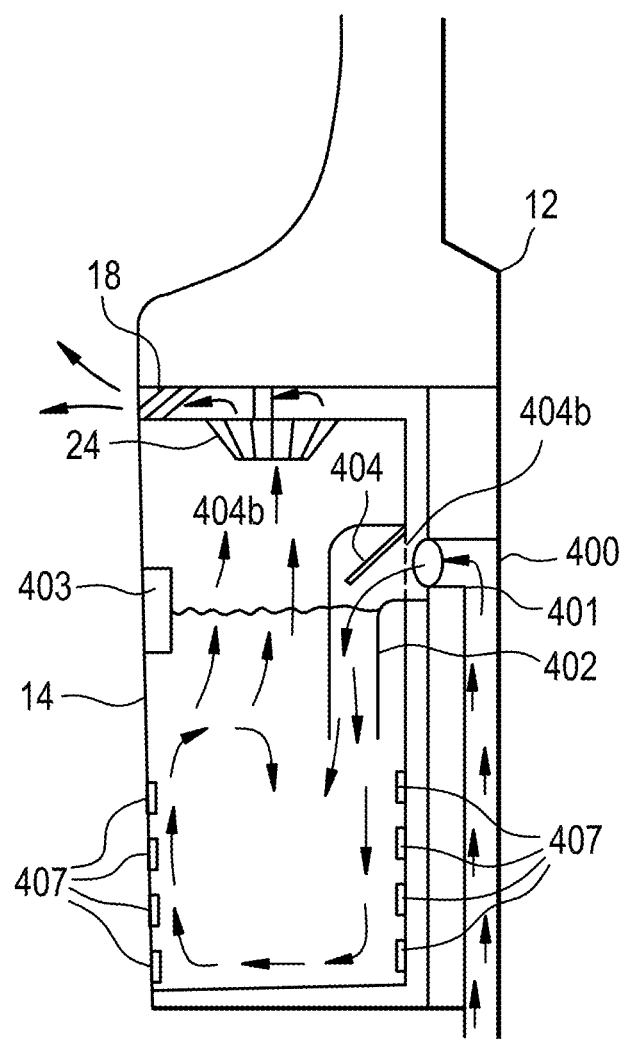

Water tank 14 can be a liquid reservoir or basin made of plastic or other materials and molded using known techniques. Liquid or dry micro silver (or nano silver) may be used as an antimicrobial component in the exemplary embodiment, although any suitable microbial agent (as discussed below) may be used. The micro or nano silver can be included into the plastic mold during processing. Any amount of micro or nano silver may be poured into the plastic mold. For example, the micro silver (or any other antimicrobial particle) may make up 1%-6% of the plastic mold. In some examples, the micro silver may make up 5% of the plastic mold. In some examples, this percentage of micro silver may allow the water tank 14 to achieve approximately 100% efficiency for killing contaminants (and/or other debris) in the water tank 14. Antimicrobial particles 407 (such as micro silver particles, nano silver particles, or any other antimicrobial particles) are shown in FIG. 6, in the wall of the water tank 14 during operation of the vacuum cleaner 10. As shown in FIG. 6, antimicrobial particles 407 are embedded into the water tank interior wall and the circulation of water (shown by arrows), including contaminants (and/or other debris), bring the contaminants (and/or other debris) into contact with the antimicrobial particles 407 to kill them.

Figure 3:
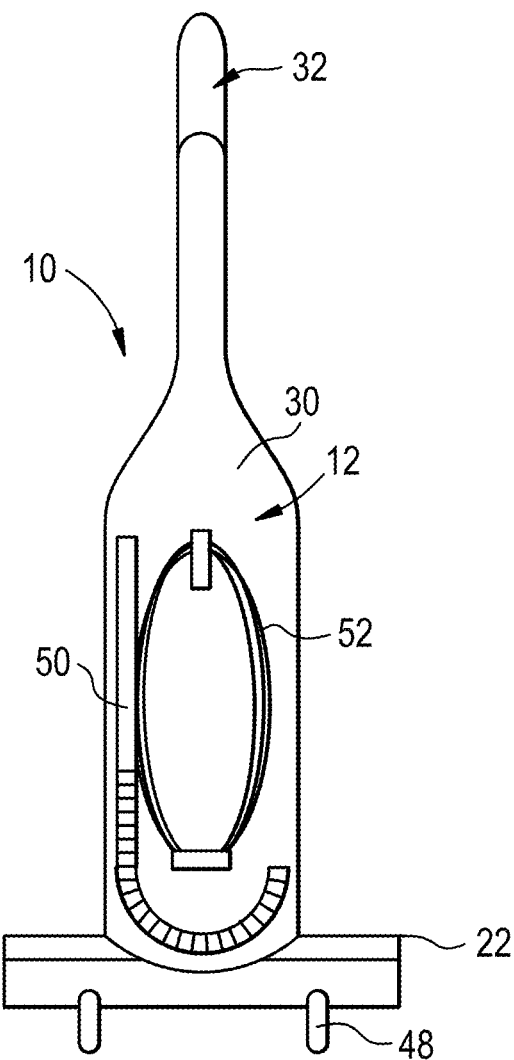

As is typical of most vacuum cleaning devices, an exemplary embodiment as shown in FIG. 3 may have a hose 50 for cleaning with attachments (not shown) in areas where the power nozzle head 22 cannot accommodate. The hose 50 may have any size, such as, for example, 5-14 feet. In some examples, the hose 50 may be 12 feet long. For suction and airflow, the hose 50 may connect with, for example, intake 400 (discussed below). Further shown is power cord 52 utilized to provide power to the vacuum cleaner 10 wrapped in typical fashion around stays. The power cord 52 may have any size, such as, for example, 15-30 feet. In some examples, the power cord may be 25 feet long.

Figure 5:
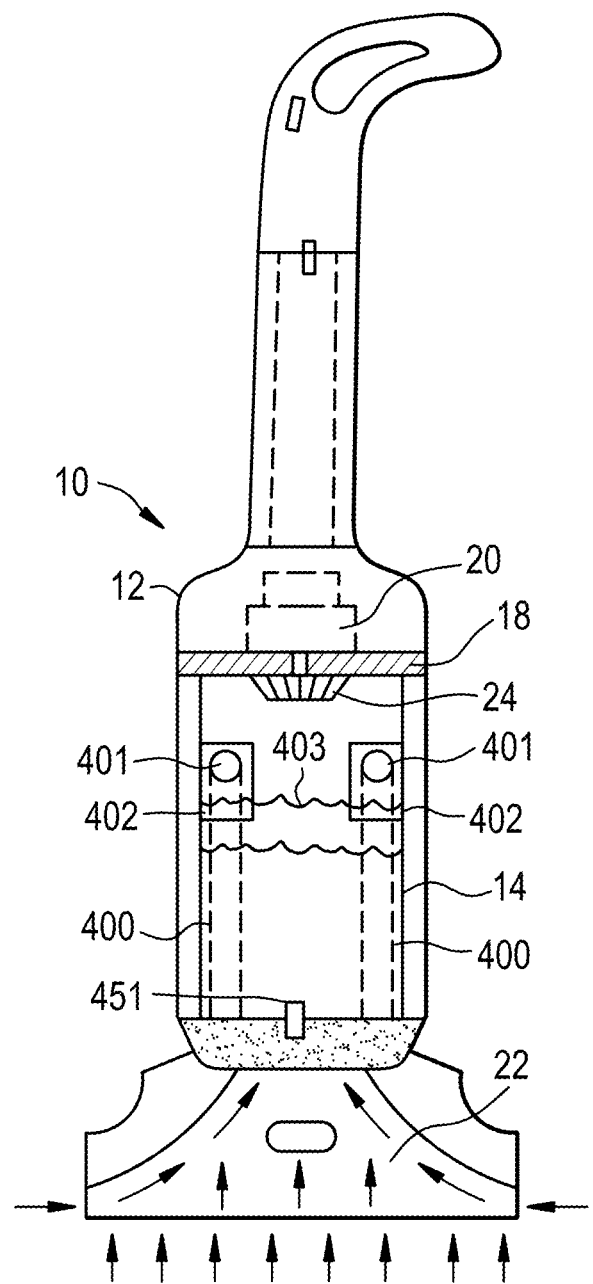

FIGS. 4 and 5 are respectively a side view and a front view of an exemplary embodiment of the water filtration vacuum cleaner 10. As shown in FIG. 4, water tank 14 is inserted into housing 12 between vacuum nozzle head 22 and motor 20. Handle 450 assists a user with inserting water tank 14 into, and removing it from housing 12. When water tank 14 is inserted into housing 12, latch 451 secures water tank 14 therein.

Motor 20 is located in the housing 12 above the water tank 14, and a separator 24 is attached to the bottom of motor 20. Separator 24 may be any device that, when operating, may generate an airflow, and that may further prevent liquid in the water tank 14 from being exhausted out of the water tank 14 through the separator 24. In some examples, separator 24 may separate air from the liquid. For example, separator 24 may draw and separate the clean exhaust air from the heavier water and particulates. This may allow the separator to prevent liquid in the water tank 14 from being exhausted out of the water tank 14 through the separator 24. Separator 24 may also force dirt and debris to mix with liquid in water tank 14.

When the water tank 14 is in place within the housing 12, separator 24 protrudes through an opening 502 (FIG. 10) on the top of water tank 14. During operation of the vacuum cleaner 10, separator 24 is rotated by the motor at high speeds, for example and without limitation, approximately 16,000 rpm, to create airflow through the vacuum cleaner 10. The motor 20 and separator 24 may generate an airflow speed (or intake velocity) of 90-130 miles per hour in each of the intakes 400 of the vacuum cleaner 10. In some examples, motor 20 and separator 24 may generate an airflow speed (or intake velocity) of 110 mph (or approximately 110 mph, such as 110 mph+/−10 mph). Air (shown by arrows) is drawn from outside the housing 12 up intake 400 on either side of the housing 12, through the water tank 14, into the separator 24, and out exhaust ports 18. Exhaust ports 18 may have any size and/or shape. Furthermore, exhaust ports 18 may be positioned at any location on the housing 12 so as to allow air to be exhausted from vacuum cleaner 10. For example, exhaust ports 18 may be positioned on a front side of the housing 12, on one or more sides of the housing 12, on the back of the housing 12, or any combination of the preceding. In some examples, exhaust ports 18 may surround all or a portion of the housing 12.

Intake 400 forms an airflow path from the vacuum nozzle head 22 to inlet port 401 on water tank 14. Inlet port 401 forms an airflow path to the interior of water tank 14. Inlet 401 and intake 400 may collectively form an intake passageway that extends from the tank intake channel 402 to an opening in the vacuum nozzle head 22, such as the opening created by inlet ports 16 in the vacuum nozzle head 22.

Inlet port 401 is above the water level 403 inside water tank 14 to prevent water from entering inlet port 401 and intake tube 400 during operation. Air exhausted from intake 400 passes through inlet port 401 and into tank intake channel 402, which directs the air into the water beneath the water level 403. The tank intake channel 402 may extend under the water level 403 by any distance. For example, the tank intake channel 402 may extend under the water level 403 by 0.1-8 inches. In some examples, the tank intake channel 402 may extend under the water level 403 by at least 3 inches (or approximately 3 inches, such as 3 inches+/−0.5 inches). This may increase the saturation of the air directed into the water.

In the front view of FIG. 5, intakes 400 are drawn in dashed lines to indicate that they are positioned behind water tank 14. Similarly, tank intake channel 402 is shown transparent to depict inlet port 401. Vacuum cleaner 10 may include any number of intakes 400 (and inlet ports 401 and tank intake channels 402). For example, the vacuum cleaner 10 may include one intake 400 (and inlet port 401 and tank intake channel 402), two intakes 400 (and inlet ports 401 and tank intake channels 402) (as is illustrated in FIG. 5), three intakes 400 (and inlet ports 401 and tank intake channels 402), four intakes 400 (and inlet ports 401 and tank intake channels 402), or any other number of intakes 400 (and inlet ports 401 and tank intake channels 402). Additionally, the intakes 400 and inlet ports 401 may be positioned in any location with regard to the water tank 14. For example, intakes 400 and inlet ports 401 may be positioned behind water tank 14, on opposite sides of the water tank 14, on the same side of the water tank 14, in front of the water tank 14, on any other location with regard to the water tank 14, or any combination of the preceding.

The flow path of the air is further detailed in FIG. 6. FIG. 6 shows a detailed view of air traveling up intake 400, into inlet port 401, past sealing flap 404 (described below), and down through tank intake channel 402 into water below water level 403 where debris can be immediately trapped and absorbed by the water. FIG. 6 shows a random flow path of air through the swirling water. In operation, forcing the airflow that contains debris below the surface of water level 403 can ensure that the debris will mix with the water and become trapped or absorbed in the water, which filters the debris from the airflow, before the airflow is exhausted from the vacuum.

The vacuum cleaner 10 may include antimicrobial particles to contact and kill contaminants (and/or other debris) and thereby provide fresh, clean, safe exhaust air to the environment. These antimicrobial particles may be positioned in the liquid bath, air flow stream, and/or embedded in the airflow pathway/componentry. As one example, the water tank 14 may include (or otherwise be formed with) embedded antimicrobials.

Antimicrobial particles may be nano particles, e.g., nano metal ions, oxides, and salts placed in the liquid bath, air flow stream, and/or embedded in the airflow pathway/componentry. Antimicrobial particles may also be micro particles, e.g., micro metal ions, oxides, and salts. Micro particles may be particles with a size within 0.1-100 μm, 0.3-300 μm, 0.7-700 μm, or any combination of the preceding. In particular examples, the micro particles may have a size of 200 μm (or approximately 200 μm, such as 200 μm+/−100 μm).

When embedded into the water tank 14, micro metal particles (such as micro silver particles) may not leach into the water. This may allow the antimicrobial properties of the water tank 14 to last longer. Additionally, this may further prevent the antimicrobial particles from being dumped into the environment (e.g., when the dirty water is emptied from the vacuum cleaner 10), which may provide various environmental benefits.

When the exemplary antimicrobials (such as a micro metal) encounter a contaminant, the micro metal oxidizes and releases ions which contact the contaminant, killing it. The antimicrobial material may further purify the airflow in a liquid bath type cleaner and provide a humidifying effect that is cleaner, healthier, and smells better than exhaust from a dry, mechanical filter.

As is illustrated in FIG. 6, antimicrobial particles 407 (such as, for example, micro silver particles, nano silver particles, any other micro metal particles, any other nano metal particles, any other antimicrobial particles, or any combination of the preceding) are embedded into a wall defining the interior volume of water tank 14. Additionally, the antimicrobial particles 407 may be embedded in any other location of the water tank 14. Contaminants (and/or other debris) in the water/air that contact the antimicrobial particles 407 are killed due to the oxidation of the antimicrobial particles 407 in the exemplary embodiment. The arrows show an arbitrary circulation path that air entering the water tank 14 may take once inside the water, including contacting the antimicrobial nanoparticles 407. Separator 24 creates the airflow for drawing the air up through intake 400, into tank 14 through inlet port 401, creating a mixing action for water in water tank 14, and drawing and separating the clean exhaust air from the heavier water and particulates.

The exemplary embodiments may achieve more efficient operation than current vacuum cleaner systems due in part to the exhaust of intake water beneath water level 403 in water tank 14, in some examples. First, debris may be immediately trapped and absorbed by the water before having a chance to be present in the headspace above the water level 403. This may allow separator 24 to draw and exhaust the clean air from the water without a separate dry, mechanical filter that is prone to clogging.

In addition, the efficiency of the liquid filter and the vacuum cleaner 10 in general may be increased, in some examples. Because there is no dry filter to clog or fail, a constant increase in efficiency of the liquid filter may be realized. Because there is no dry filter to clog or fail, the vacuum cleaner 10 can have a constant and consistent airflow at all points throughout the vacuum from the initial air intake to the exhaust. As a result, the efficiency of the vacuum cleaner may be increased, allowing a higher average intake velocity and a greater volume of airflow through the unit, in some examples. Also, the vacuum cleaner 10 may include more than one intake 400, inlet port 401, and tank intake channel 402 (such as two or more intakes 400, inlet ports 401, and tank intake channels 402), which may allow more air (and dirt and debris) to enter the vacuum cleaner 10 and further increase the efficiency of the vacuum cleaner 10, in some examples.

Another benefit of the current exemplary embodiment of the vacuum cleaner 10 is that it will resist (or prevent) spills and leaks. For example, the vacuum cleaner 10 may be able to seal the intakes 400, inlet ports 401, and/or tank intake channels 402 when the vacuum cleaner is deactivated (such as when the separator 24 is not generating airflow). This may prevent liquid in the water tank 14 from leaking out of the water tank 14 through the intakes 400, inlet ports 401, and/or tank intake channels 402. Additionally, the vacuum cleaner 10 may further be able to unseal the intakes 400, inlet ports 401, and/or tank intake channels 402 when the vacuum cleaner is activated (such as when the separator 24 is generating airflow).

Figure 7:
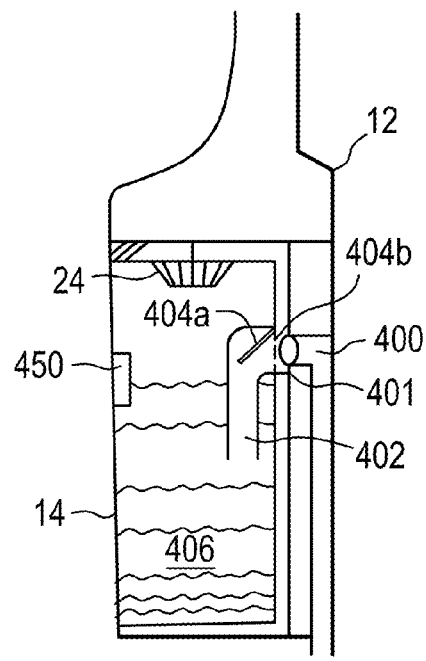

In one example, vacuum cleaner 10 may be able to seal and unseal the intakes 400, inlet ports 401, and/or tank intake channels 402 using sealing flaps 404 shown in FIGS. 4-7. With reference now to FIGS. 4-7, water tank 14 includes sealing flap 404 for closing inlet port 401 within the air intake passages to prevent leaks when the vacuum cleaner 10 is not operating. When the vacuum cleaner 10 is operating (or activated), the air flow from intake 400 to tank intake channel 402 (and/or an automated flap mover 500, discussed below) forces sealing flap 404 open, allowing air to pass through and down into the liquid in water tank 14 via tank intake channel 402. FIG. 7 shows the sealing flap 404 in open 404a and closed 404b (dashed line) configurations. When the vacuum cleaner 10 is not operating (or deactivated), e.g., there is no airflow through intake 400, sealing flap 404 is forced to the closed configuration 404b by a flap movement resistor 405 (such as one or more springs) shown in FIGS. 8 and 9 (and/or the automated flap mover 500 shown in FIG. 10). When the vacuum cleaner 10 is operating and there is airflow through intake tube 400 and inlet port 401, the force of the airflow (and/or the force of the flap movement resistor 500) may overcome the strength (or force) of the flap movement resistor 405 and urges the sealing flap 404 to the open position 404a as depicted in FIGS. 4 and 6.

By closing (and remaining closed) when the vacuum cleaner 10 is not operating, the sealing flap 404 may prevent liquid from leaking out of intake 400, thereby resisting spills and leaks of the liquid. The closed sealing flap 404 may prevent such leaks even when the vacuum cleaner 10 is tipped or tilted. For example, the closed sealing flap 404 may prevent such leaks even when the housing 12 (and water tank 14) is tilted at tilt angle 21 with respect to the vacuum nozzle head 22. This may allow the housing 12 (and water tank 14) to be tilted to, for example, a horizontal position, while still preventing spills and leaks of the liquid. In some examples, such an ability may allow a liquid filter to be used in an upright-style vacuum cleaner.

The closed sealing flap 404 may also prevent leaks even when the vacuum cleaner 10 is moved. For example, the closed sealing flap 404 may prevent such leaks even when the vacuum cleaner 10 is moved around in any direction, at any speed, and/or on any surface type, or even when the vacuum cleaner 10 is picked up and carried around. Despite this movement possibly causing the liquid in water tank 14 to slosh around (and even violently slosh around) inside of the water tank 14, the closed sealing flap 404 may prevent the liquid from leaking out of the water tank 14 through intake 400.

Figure 8:
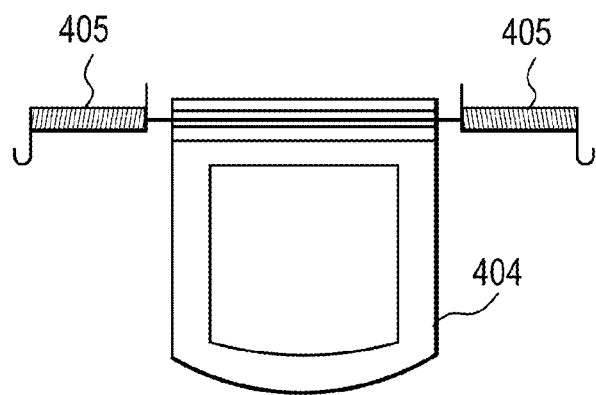
Figure 9:

In the exemplary embodiment shown by FIGS. 7-9, sealing flap 404 is made from rubber and is generally U-shaped with two flap movement resistors 405 (such as springs) attached to the top of the 'U'. The flap movement resistors 405 are also attached to the wall of the water tank 14 proximate inlet port 401.

A flap movement resistor 405 may be any device and/or structure that may resist movement of the sealing flap 404 from a closed position (404b) to an open position (404a). By doing so, the flap movement resistor 405 may urge the sealing flap 404 towards the inlet port 401 (e.g., it may urge the sealing flap 405 to a closed position). Examples of a flap movement resistor 405 include a spring, a resilient material, counterweights, magnetic attachments, mechanical devices, any other device and/or structure that may resist movement (and/or that may urge movement in an opposite direction), or any combination of the preceding. As is illustrated, the flap movement resistors 405 include springs.

In the absence of an opposing force, the flap movement resistor(s) 405 may cause sealing flap 404 to seal against inlet port 401 and/or intake tube 400 as shown in the closed configuration 404b of FIG. 5. Thus, when the vacuum cleaner 10 is not in operation, sealing flap 404 will prevent water from leaking out of the water tank 14 through the inlet port 401 and/or intake 400 even if the vacuum cleaner 10 is tipped or tilted.

The flap movement resistors 405 may have any strength (or force) for resisting movement and/or for urging the sealing flap 404 towards the inlet port 401. For example, the flap movement resistors 405 may have a strength of 1-2 pounds pressure. As an example of this, the flap movement resistors 405 may be 1-2 pound pressure springs. As another example, the flap movement resistors 405 may have a strength of 0.5-3 pounds pressure. As an example of this, the flap movement resistors 405 may be 0.5-3 pound pressure springs.

Although the sealing flap 404 has been illustrated in FIG. 7 as sealing off the entry/exit point of the inlet port 401, the sealing flap 404 may seal off any other portion of the inlet port 401 or seal off any other component of the vacuum cleaner 10 so as to prevent water from leaking out of intake 400. For example, the sealing flap 404 may be positioned at the end of the tank intake channel 402 (or any other location in the tank intake channel 402) so as to seal off the tank intake channel 402. As another example, the sealing flap 404 may be positioned within the inlet port 401 so as to seal off the inlet port 401. As a further example, the sealing flap 404 may be positioned at the intersection between the inlet port 401 and the intake 400 (or any other location within the intake 400) so as to seal off the intake 400.

Additionally, vacuum cleaner 10 may include any number of sealing flaps 404 to prevent water from leaking out of an intake 400. For example, two or more sealing flaps 404 may be positioned in series with each other along the tank intake channel 402, the inlet port 401, and/or the intake 400. In such an example, if liquid were to leak past a first sealing flap 404 (such as, for example, a sealing flap 404 sealing off the inlet port 401), the liquid may be prevented from leaking out of intake 400 by a second sealing flap 404 (such as, for example, a sealing flap 404 sealing off the intake 400).

Furthermore, vacuum cleaner 10 may include one or more sealing flaps 404 for each passageway into the liquid in water tank 14. For example, vacuum cleaner 10 may include one or more sealing flaps 404 for a first passageway into the liquid in water tank 14 (where the passageway includes an intake 400, an inlet port 401, and a tank intake channel 402 in fluid communication with each other), and may also include one or more sealing flaps 404 for each additional passageway into the liquid in water tank 14 (where each additional passageway also includes an intake 400, an inlet port 401, and a tank intake channel 402 in fluid communication with each other).

In the exemplary embodiment, sealing flap 404 includes a rubber gasket (not shown) configured to seal against intake 400, inlet port 401, and/or tank intake channel 402. Although sealing flap 404 has been described above as having a particular configuration, in other embodiments, sealing flap 404 may have any configuration (such as any size and/or shape) and may be made from any known material(s) suitable for use consistent with this disclosure, for example and without limitation, plastics, laminates, or foams.

The flap movement resistor(s) 405 may be coupled to the sealing flap 404 and other components by any suitable means such as adhesives, welding, molding, etc. In some embodiments, to couple the flap movement resistor 405 to the sealing flap 404, the flap movement resistor 405 may be formed integral to the sealing flap 404, such as a sealing flap 404 made from a resilient or elastic material. In the same or other embodiments, the sealing flap 404 and/or flap movement resistor 405 may be formed integral to, e.g., the water tank 14, inlet port 401, and/or intake 400, for example as a hinged mechanism formed on one of the components.

Figure 10:
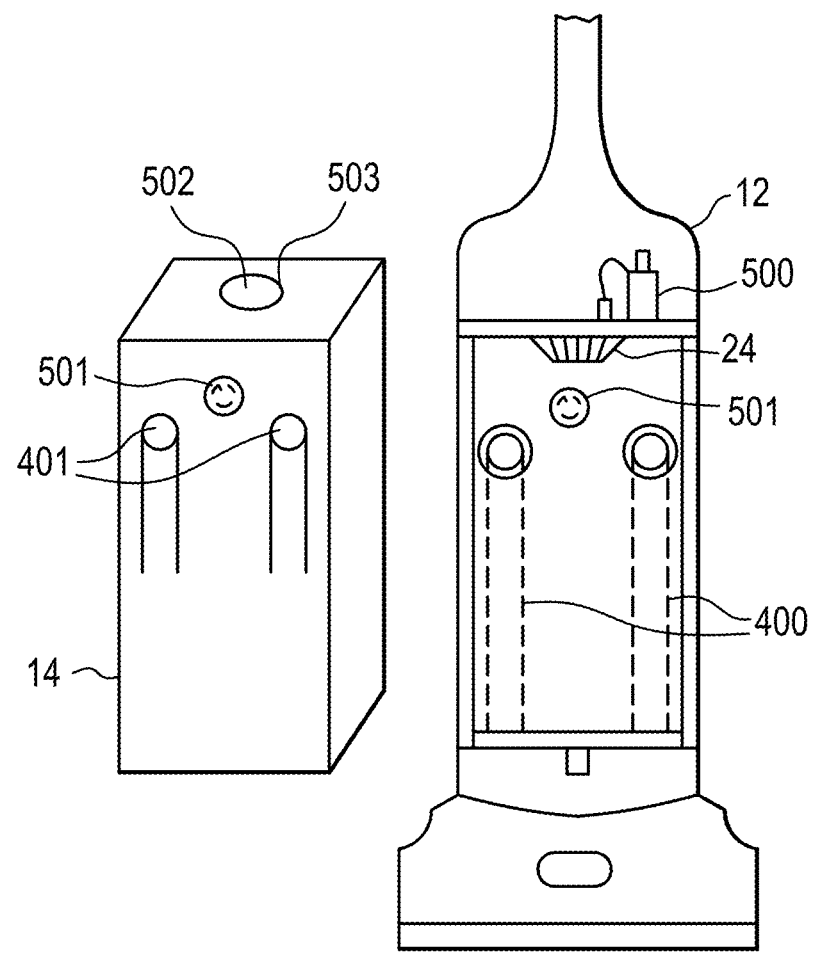
FIG. 10 is a view of an example water tank detached from the housing of the vacuum cleaner of FIG. 1.

FIG. 10 shows another example of a sealing flap 404 assembly. As shown in FIG. 10, an automated flap mover 500 is provided in housing 12 and is electrically connected to socket 501 on housing. When water tank 14 is inserted into housing 12, sockets 501 connect, thereby providing a pathway to provide power to the automated flap mover 500. When switch 34 is activated (turning on motor 20 and causing separator 24 to generate airflow), power is provided to the automated flap mover 500. This will cause the automated flap mover 500 to move the sealing flap 404 from the closed position 404b to the open position 404a. Additionally, when the switch 34 is deactivated (or the vacuum cleaner 10 loses power, such as if the power plug is pulled from an electrical outlet), the automated flap mover 500 will move the sealing flap 404 from the open position 404a to the closed position 404b. The automated flap mover 500 will keep the sealing flap 404 in the closed position 404b until the switch 34 is once again activated (or the motor 20 and separator 24 are otherwise turned on). This may prevent liquid from leaking out of intakes 400 even if the vacuum cleaner 10 is tipped or tilted.

Automated flap mover 500 may be any device and/or structure that may move sealing flap 404. For example, automated flap mover 500 may be a solenoid, a solenoid valve, a motorized lever, any other mechanical device for causing movement, any other electro/mechanical device for causing movement, any other device and/or structure for causing automated movement, or any combination of the preceding. Vacuum cleaner 10 may include any number of automated flap movers 500. For example, vacuum cleaner 10 may include one automated flap mover 500 for each sealing flap 404. As another example, vacuum cleaner 10 may include one automated flap mover 500 for all of the sealing flaps 404, or for a set of sealing flaps 404.

In some examples, the automated flap mover 500 may be the only component that opens and closes the sealing flap 404. In such examples, the sealing flap 404 may not include flap movement resistors 405 for resisting movement of the sealing flap 404 (and/or for urging the sealing flap 404 closed). Additionally, in such examples, the sealing flap 404 may not be opened by the airflow (or intake velocity) generated by motor 20 and separator 24.

In other examples, the sealing flap 404 may be opened and closed by the automated flap mover 500, but the sealing flap 404 may also be opened by the airflow, and the sealing flap 404 may include flap movement resistors 405 for resisting movement of the sealing flap 404 (and/or for urging the sealing flap 404 closed). In such examples, the automated flap mover 500 may be the primary component for opening and closing the sealing flap 404, and the airflow and the flap movement resistors 405 may be a back-up. If the automated flap mover 500 were to stop operating, the sealing flap 404 would still be able to open and close using the airflow and the flap movement resistors 405. Furthermore, even when the automated flap mover 500 is operating, the flap movement resistors 405 may assist in closing the sealing flap 404. Alternatively, the automated flap mover 500 may be the back-up mechanism for opening and closing the sealing flap 404, and the airflow and the flap movement resistors 405 may be the primary mechanism. If the airflow were to fail to open the sealing flap 404 (and/or the flap movement resistors 405 were to fail to close the sealing flap 404), the automated flap mover 500 could open and/or close the sealing flap 404.

In further examples, the sealing flap 500 may be opened by the automated flap mover 500, but not closed by the automated flap mover 500 (or vice versa). In such examples, the sealing flap 404 may be closed by the flap movement resistors 405 (or the sealing flap 404 could be opened by the airflow).

In further examples, the vacuum cleaner 10 may not include an automated flap mover 500 for opening and closing the sealing flaps 404. In such an example, the sealing flaps 404 may be opened entirely by the airflow and the sealing flaps 404 may be closed entirely by the flap movement resistors 405. In such an example, the strength of the flap movement resistors 405 may be less than 1-2 pounds pressure.

As previously indicated, FIG. 10 further depicts opening 502 on top of water tank 14. Opening 502 may be used to empty and fill water tank 14, but is also configured to accept separator 24 when the water tank 14 is inserted into housing 12. Water tank opening 502 includes a raised lip 503 in an exemplary embodiment for sealing against a motor gasket 25 as will be explained with respect to FIGS. 9-11. In other embodiments, opening 502 may be sealed in any other manner suitable for creating a water-tight seal, such as frictional engagements, slotted grooves, o-rings, etc. In general, the centrifugal force generated by separator 24 while vacuum cleaner 10 is in operation is sufficient to deflect any water away from the motor 20 assembly seal.

Figure 11:
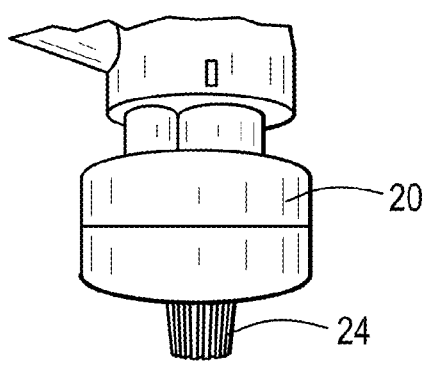
FIG. 11 is a view of an example motor of the vacuum cleaner of FIG. 1.
Figure 12:
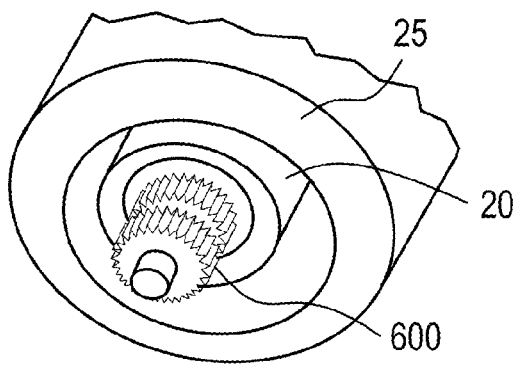
FIG. 12 is a detailed view of the motor of FIG. 11.
Figure 13:
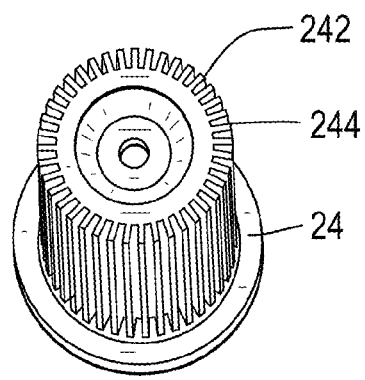
FIG. 13 is a detailed view of an example separator of the vacuum cleaner of FIG. 1.

FIGS. 11-13 show additional details regarding the coupling between the motor 20 and the separator 24. As shown in FIG. 11, separator 24 extends away from a bottom of motor 20. Separator 24 is shown in FIG. 13. The ribs 242 and grooves 244 of separator 24 (FIG. 13) create the required airflow for the vacuum cleaner 10 during operation when the separator is rotating. FIG. 12 shows the bottom of motor 20 including gears 600 and gasket 25. During operation, separator 24 is connected to gears 600 such that motor 20 rotates separator 24.

Lip 503 around opening 502 (as illustrated in FIG. 10) on the top of water tank 14 is configured to engage the motor gasket 25 and seal the water tank 14 to the motor 20 when the water tank 14 is inserted in housing 12.

Figure 14:
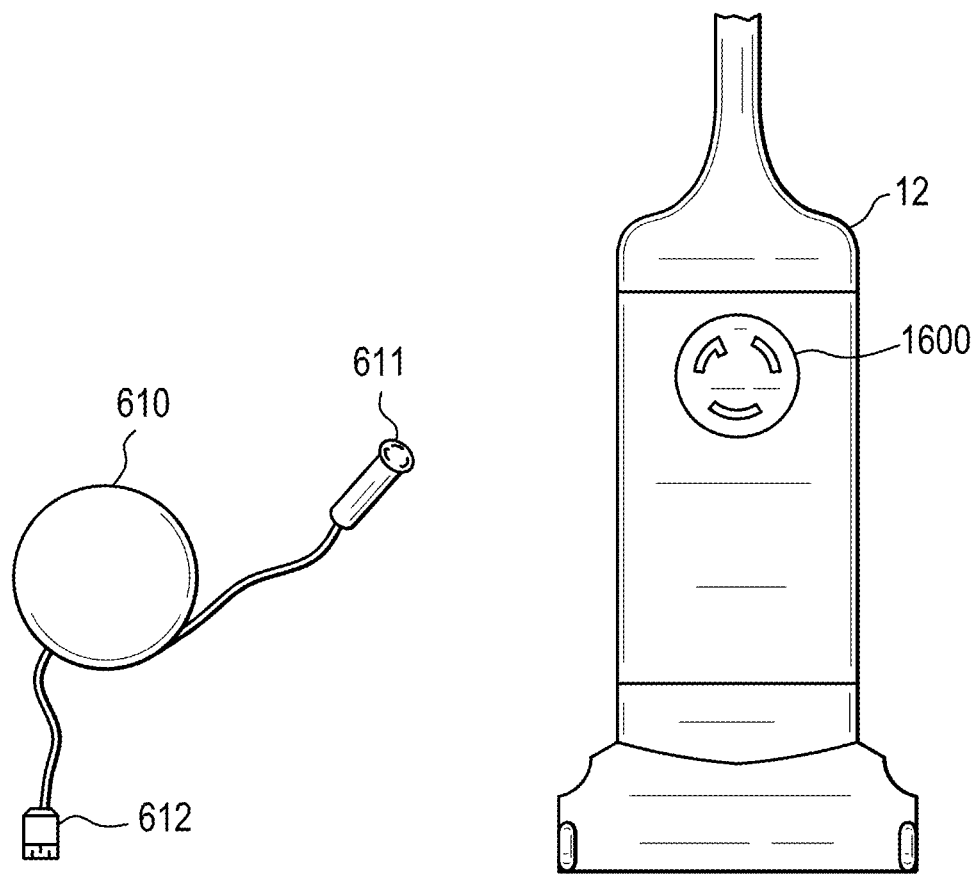
FIG. 14 is a view of an example power supply of the vacuum cleaner of FIG. 1.

FIG. 14 shows an exemplary removable power connection for the vacuum cleaner 10. The back of housing 12 includes a circular connector 1600 in an exemplary embodiment that mates with a female circular connector 611 on a retractable power cord organizer 610. On an opposite end is a wall outlet 612 (such as a standard 120V wall outlet), which may be unplugged or left plugged in when a user is finished using the vacuum cleaner 10. Retractable power cord organizer 610 is removable from the housing 12, and reattached as discussed above. Any other power connection may be used with the vacuum cleaner 10.

FIG. 15 shows a side view of a vacuum cleaner that can operate as a wet vacuum. As is illustrated, the vacuum cleaner 10 is an upright-style vacuum that can operate as a wet vacuum. When the vacuum cleaner 10 is operating, the vacuum nozzle head 22 (or the hose of the vacuum cleaner 10) may be positioned over liquid (such as water) or a combination of liquid and a dry debris or dirt. The airflow and suction created by the motor 20 and separator 24 may then perform liquid extraction (or water extraction) by drawing the liquid (or liquid and dry debris or dirt) into intake 400. As is illustrated in FIG. 15, the extracted liquid may travel up intake 400, into inlet port 401, past sealing flap 404 (described above), and down through tank intake channel 402 into water tank 14, such as into water below water level 403 in water tank 14. Separator 24 may draw and separate the clean exhaust air from the extracted liquid and any dry debris or dirt. While the clear exhaust air may pass through the separator 24, the extracted liquid may remain in water tank 14. This may prevent the extracted liquid from causing damage to one or more components of the vacuum cleaner 10, and thereby allow the vacuum cleaner 10 to operate as a wet vacuum.

In contrast to vacuum cleaner 10, traditional upright-style vacuum cleaners may not operate as wet vacuums because the extracted liquid may be sucked into the motor of the traditional upright-style vacuum cleaner. Not only may this break the traditional upright-style vacuum cleaner, but it may also cause an electrical shock to the user of the traditional upright-style vacuum cleaner.

In some examples, the liquid extraction performed by the vacuum cleaner 10 may allow the water tank 14 to be filled without removing the water tank 14 from the housing 12. For example, instead of removing water tank 14 from the housing 12 and using opening 502 (FIG. 10) to fill the water tank 14, the vacuum cleaner 10 may be positioned over water (or other liquid). The airflow and suction of the vacuum cleaner 10 will extract the water and fill the water tank 14, as is discussed above.

Although the vacuum cleaner 10 of FIG. 15 has been described above as operating as a wet vacuum, in some examples the vacuum cleaner 10 of FIG. 15 may also operate as a dry vacuum, as is discussed above with regard to FIG. 1-14. In such examples, the vacuum cleaner 10 may direct a non-liquid matter (such as air, which may include dirt or debris) into the water tank 14. Thus, the vacuum cleaner 10 of FIG. 15 may operate as both a dry vacuum and a wet vacuum.

Modifications, additions, combinations, or omissions may be made to the upright vacuum cleaner 10 (and/or any of the components of the upright vacuum cleaner 10) without departing from the scope of the disclosure. For example, although vacuum cleaner 10 has been described above as directing incoming air directly into the liquid bath filter, in some examples the incoming air may be directed into a headspace above the liquid level, or a portion of the incoming air could be directed directly into the liquid bath filter and a portion of the incoming air could be directed into the headspace above the liquid level. In such examples, the separator 24 may cause the air in the head space to be pulled down into the liquid by aspiration due to circulation or agitation of the liquid. As another example, although vacuum cleaner 10 has been described above as not including a dry, mechanical filter, in some examples the vacuum cleaner 10 may include one or more dry, mechanical filters. These dry, mechanical filters may further assist in filtering the air sucked through the vacuum cleaner 10.

This specification has been written with reference to various non-limiting and non-exhaustive embodiments or examples. However, it will be recognized by persons having ordinary skill in the art that various substitutions, modifications, or combinations of any of the disclosed embodiments or examples (or portions thereof) may be made within the scope of this specification. Thus, it is contemplated and understood that this specification supports additional embodiments or examples not expressly set forth in this specification. Such embodiments or examples may be obtained, for example, by combining, modifying, or reorganizing any of the disclosed steps, components, elements, features, aspects, characteristics, limitations, and the like, of the various non-limiting and non-exhaustive embodiments or examples described in this specification. In this manner, Applicant reserves the right to amend the claims during prosecution to add features as variously described in this specification.

The invention claimed is:

1. An upright liquid filtration vacuum cleaner, comprising:
   vacuum nozzle head having a first motor coupled to a rotatable brush;
   a housing moveably coupled to the vacuum nozzle head, the movable coupling configured to allow the housing to tilt backwards with respect to the vacuum nozzle head from a substantially upright position to a substantially horizontal position;
   a liquid tank that is removably insertable into the housing, the liquid tank comprising:
      a wall defining an interior volume, the interior volume configured to hold a liquid, the wall having micro silver particles embedded in the wall;
      a first tank intake channel positioned in the interior volume, the first tank intake channel being in fluid communication with a first intake passageway that extends from the first tank intake channel to an opening in the vacuum nozzle head, the first tank intake channel further being positioned to direct debris received from the first intake passageway to below a liquid level of the liquid; and
      a second tank intake channel positioned in the interior volume, the second tank intake channel being in fluid communication with a second intake passageway that extends from the second tank intake channel to the opening in the vacuum nozzle head, the second tank intake channel further being positioned to direct debris received from the second intake passageway to below the liquid level of the liquid;
      wherein the liquid in the interior volume of the liquid tank filters the debris into the liquid so that clean air is exhausted;
   a first sealing flap positioned at a location in the first intake passageway, the first sealing flap having a first position configured to seal the first intake passageway so as to prevent the liquid from leaking out of the interior volume of the liquid tank through the first intake passageway, the first sealing flap having a second position configured to open the seal of the first intake passageway so as to allow the debris to be received in the interior volume of the liquid tank from the first intake passageway;
   a second sealing flap positioned at a location in the second intake passageway, the second sealing flap having a first position configured to seal the second intake passageway so as to prevent the liquid from leaking out of the interior volume of the liquid tank through the second intake passageway, the second sealing flap having a second position configured to open the seal of the second intake passageway so as to allow the debris to be received in the interior volume of the liquid tank from the second intake passageway;
   a second motor coupled to the housing;
   a separator coupled to the housing and the motor, the separator being in fluid communication with the interior volume of the liquid tank, the separator being configured to generate an airflow and further configured to separate air from the liquid so as to prevent the liquid from being exhausted out of the interior volume of the liquid tank through the separator;
   a solenoid configured to move both the first sealing flap and the second sealing flap from the first position configured to seal the first and second intake passageways so as to prevent the liquid from leaking out of the interior volume of the liquid tank through the first and second intake passageways to the second position configured to open the seal of the first and second intake passageways so as to allow the debris to be received in the interior volume of the liquid tank from the first and second intake passageways;
   a first spring coupled to the first sealing flap and a second spring coupled to the second sealing flap, wherein the springs are each configured to resist the movement of the respective sealing flap from the first position to the second position, wherein the strength of each springs is configured to be overcome by the solenoid, the airflow, or both the solenoid and the airflow;
   wherein the vacuum cleaner is configured to operate as a wet vacuum in which the debris comprises a liquid to be extracted; and
   wherein the vacuum cleaner is further configured to operate as a dry vacuum in which the debris comprises a non-liquid matter.

2. An upright liquid filtration vacuum cleaner, comprising:
   vacuum nozzle head;
   a housing moveably coupled to the vacuum nozzle head, the movable coupling configured to allow the housing to tilt backwards with respect to the vacuum nozzle head;
   a liquid tank that is removably insertable into the housing, the liquid tank comprising:
      a wall defining an interior volume, the interior volume configured to hold a liquid; and
      a tank intake channel positioned in the interior volume, the tank intake channel being in fluid communication with an intake passageway that extends from the tank intake channel to an opening in the vacuum nozzle head, the tank intake channel further being positioned to direct debris received from the intake passageway to below a liquid level of the liquid;
   a sealing flap positioned at a location in the intake passageway, the sealing flap having a first position configured to seal the intake passageway so as to prevent the liquid from leaking out of the interior volume of the liquid tank through the intake passageway, the sealing flap having a second position configured to open the seal of the intake passageway so as to allow the debris to be received in the interior volume of the liquid tank from the intake passageway;
   wherein the liquid in the interior volume of the liquid tank filters the debris into the liquid so that clean air is exhausted;
   a motor coupled to the housing;
   a separator coupled to the housing and the motor, the separator being in fluid communication with the interior volume of the liquid tank, the separator being configured to generate an airflow and further configured to prevent the liquid from being exhausted out of the interior volume of the liquid tank through the separator;
   wherein the vacuum cleaner is configured to move the sealing flap from the first position to the second position when the vacuum cleaner is activated, and the vacuum cleaner is further configured to move the sealing flap from the second position to the first position when the vacuum cleaner is deactivated;
   wherein the vacuum cleaner is configured to operate as a wet vacuum in which the debris comprises a liquid to be extracted; and wherein the vacuum cleaner is further configured to operate as a dry vacuum in which the debris comprises a non-liquid matter.

3. The vacuum cleaner of claim 2, wherein the wall of the water tank includes antimicrobial particles.

4. The vacuum cleaner of claim 3, wherein the antimicrobial particles comprise micro silver particles.

5. The vacuum cleaner of claim 3, wherein the antimicrobial particles comprise nano silver particles.

6. The vacuum cleaner of claim 2, wherein:
the liquid tank further comprises a second tank intake channel positioned in the interior volume, the second tank intake channel being in fluid communication with a second intake passageway that extends from the second tank intake channel to the opening in the vacuum nozzle head, the second tank intake channel further being positioned to direct debris received from the second intake passageway to below the liquid level of the liquid;
the vacuum cleaner further includes a second sealing flap positioned at a location in the second intake passageway, the second sealing flap having a first position configured to seal the second intake passageway so as to prevent the liquid from leaking out of the interior volume of the liquid tank through the second intake passageway, the second sealing flap having a second position configured to open the seal of the second intake passageway so as to allow the debris to be received in the interior volume of the liquid tank from the second intake passageway; and
the vacuum cleaner is further configured to move the second sealing flap from the first position to the second position when the vacuum cleaner is activated, and the vacuum cleaner is further configured to move the second sealing flap from the second position to the first position when the vacuum cleaner is deactivated.

7. The vacuum cleaner of claim 6, wherein both the intake passageway and the second intake passageway are positioned in the housing in locations behind the water tank.

8. The vacuum cleaner of claim 6, wherein the intake passageway and the second intake passageway are positioned in the housing in locations opposite from each other.

9. The vacuum cleaner of claim 2, further comprising an automated flap mover configured to move the sealing flap from the first position configured to seal the first intake passageway so as to prevent the liquid from leaking out of the interior volume of the liquid tank through the intake passageway to the second position configured to open the seal of the intake passageway so as to allow the debris to be received in the interior volume of the liquid tank from the intake passageway.

10. The vacuum cleaner of claim 9, wherein the automated flap mover comprises a solenoid.

11. The vacuum cleaner of claim 9, further comprising one or more movement resistors coupled to the sealing flap and configured to resist the movement of the sealing flap from the first position to the second position, wherein the strength of the one or more movement resistors is configured to be overcome by the automated flap mover, the airflow, or both the automated flap mover and the airflow.

12. The vacuum cleaner of claim 2, further comprising one or more movement resistors coupled to the sealing flap and configured to resist the movement of the sealing flap from the first position to the second position, wherein the strength of the one or more movement resistors is configured to be overcome by the airflow.

13. The vacuum cleaner of claim 12, wherein the one or more movement resistors comprise one or more springs.

14. The vacuum cleaner of claim 2, wherein the vacuum nozzle head is a power nozzle with a second motor coupled to a rotatable brush.

15. The vacuum cleaner of claim 2, wherein the movable coupling is further configured to allow the housing to tilt backwards with respect to the vacuum nozzle head from a substantially upright position to a substantially horizontal position without liquid escaping the liquid tank.

16. An upright liquid filtration vacuum cleaner, comprising:
vacuum nozzle head;
a housing moveably coupled to the vacuum nozzle head, the movable coupling configured to allow the housing to tilt backwards with respect to the vacuum nozzle head;
a liquid tank that is removably insertable into the housing, the liquid tank comprising:
a wall defining an interior volume, the interior volume configured to hold a liquid; and
a tank intake channel positioned in the interior volume, the tank intake channel being in fluid communication with an intake passageway that extends from the tank intake channel to an opening in the vacuum nozzle head, the tank intake channel further being positioned to direct debris received from the intake passageway into the liquid tank;
wherein the liquid in the interior volume of the liquid tank filters the debris into the liquid so that clean air is exhausted;
a motor coupled to the housing;
a separator coupled to the housing and the motor, the separator being in fluid communication with the interior volume of the liquid tank, the separator being configured to generate a airflow and further configured to prevent the liquid from being exhausted out of the interior volume of the liquid tank through the separator;
wherein the vacuum cleaner is configured to seal the intake passageway when the vacuum cleaner is deactivated so as to prevent the liquid from leaking out of the interior volume of the liquid tank through the intake passageway, and the vacuum cleaner is further configured to unseal the intake passageway when the vacuum cleaner is activated so as to allow the debris to be received in the interior volume of the liquid tank from the intake passageway;
wherein the vacuum cleaner is configured to operate as a wet vacuum in which the debris comprises a liquid to be extracted; and
wherein the vacuum cleaner is further configured to operate as a dry vacuum in which the debris comprises a non-liquid matter.

17. The vacuum cleaner of claim 16, wherein the vacuum cleaner is devoid of a dry, mechanical filter.

18. The vacuum cleaner of claim 17, further comprising a dry, mechanical filter.

19. The vacuum cleaner of claim 16, wherein the tank intake channel is further positioned to direct the debris received from the intake passageway to below a liquid level of the liquid.

20. The vacuum cleaner of claim 16, wherein the tank intake channel is further positioned to direct the debris received from the intake passageway to above a liquid level of the liquid.

* * * * *